United States Patent [19]

Schwartz

[11] Patent Number: 4,939,252
[45] Date of Patent: Jul. 3, 1990

[54] NOVEL INTERMEDIATES FOR THE PREPARATION OF CARBOVIR

[75] Inventor: Alan Schwartz, Upper Montclair, N.J.

[73] Assignee: Hoffmann-La Roche Inc., Nutley, N.J.

[21] Appl. No.: 340,648

[22] Filed: Apr. 20, 1989

[51] Int. Cl.$^5$ .................. C07D 239/30; C07D 239/50
[52] U.S. Cl. .................................... 544/321; 544/320; 544/276
[58] Field of Search ........................ 544/320, 321, 276

[56] References Cited

U.S. PATENT DOCUMENTS 4,339,453  7/1982  Grier et al. ........................ 540/320
4,742,064  5/1988  Vince ................................. 544/276
4,857,531  8/1989  Borthwick et al. ................ 544/276

FOREIGN PATENT DOCUMENTS 178178  4/1986  European Pat. Off. .

OTHER PUBLICATIONS

Vince et al., Biochemical & Biophysical Research Comm. vol. 156, No. 2, 1988, pp. 1046–1053.
Constant et al., J. Heterocyclic Chem. 22:1035 (1985).
Costin et al. Chem. Abst. 51–1973e (1957).
Logemann et al., Chem. Abst. 53–18053b (1959).
Fischer et al., Chem. Ber. 85, p. 752 (1952).
Bogert et al., JACS, vol. 55. p. 1667 (1933).

Primary Examiner—Cecilia Shen
Attorney, Agent, or Firm—George M. Gould; William H. Epstein; Patricia S. Rocha

[57] ABSTRACT

The invention provides novel cyclopentenyl carbinol compounds which are useful as intermediates for the preparation of the anti-AIDS drug, Carbovir. Processes for the preparation of such novel compounds and for the use of the compounds to make Carbovir are also provided.

6 Claims, No Drawings

NOVEL INTERMEDIATES FOR THE PREPARATION OF CARBOVIR

TECHNICAL FIELD

This invention relates to novel synthetic processes and chemical intermediates for the preparation of Carbovir, carbocyclic 2',3'-didehydro-2',3'-dideoxyguanosine.

BACKGROUND OF THE INVENTION

The rapid spread of acquired immune deficiency syndrome (AIDS) throughout the world has led to intensive efforts develop therapeutic agents to cure or at least ameliorate the disease. Most chemical agents developed to this point have been nucleoside analogs, which may interfere with the replication of the human immunodeficiency viruses (HIV) believed to be responsible for AIDS.

The best known of these nucleoside analogs are 3'-azido-2',3'-dideoxythymidine (AZT), the only drug currently approved in the United States for AIDS therapy, and dideoxycytidine, which is undergoing clinical trials. More recently, Vince et al. [Biochem. Biophys. Res. Commun. 156:1046 (1988)] have described a carbocyclic nucleoside analog of guanosine that is a potent and selective inhibitor of HIV replication in vitro. This analog, carbocyclic 2',3'-didehydro-2',3'-dideoxyguanosine, is commonly known as Carbovir.

SUMMARY OF THE INVENTION

This invention provides novel intermediates for the synthesis of Carbovir, processes for preparing such intermediates and processes for the synthesis of Carbovir which utilize these intermediates. Through the use of the intermediates and processes of the invention, Carbovir can be made more simply and in a much higher yield than has heretofore been possible.

More particularly, this invention provides a process for producing (±)-(1α,4α)-4-[(2-Amino-5-nitro-6(1H)-pyrimidinore)-amino]-2-cyclopentenyl carbinol, having the formula

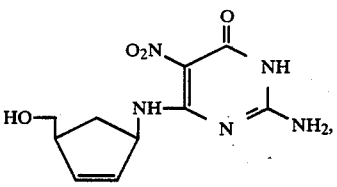

III comprising reacting a compound of the formula

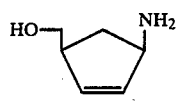

I with a compound of the formula

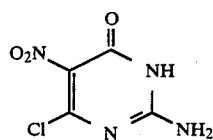

II in a polar aprotic solvent in the presence of a tertiary alkylamine.

This invention further provides a process for producing (±)-(1α,4α)-4-[2,5-Diamino-6(1H)-pyrimidinore)-amino]-2-cyclopentenyl carbinol, having the formula

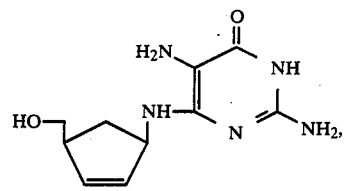

IV comprising treating a compound of the formula

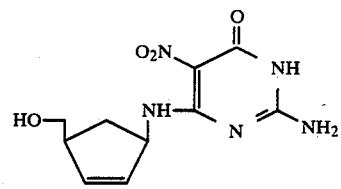

III with aqueous sodium dithionite in the presence of an alkanol and a polar aprotic solvent under reflux to reduce the nitro group of such compound to an amino group.

This invention still further provides a process for producing Carbovir, comprising:

(a) treating a compound of the formula

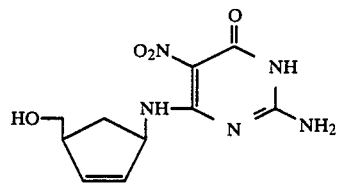

III with aqueous sodium dithionite in the presence of an alkanol and a polar aprotic solvent under reflux to reduce the nitro group of such compound to an amino group and produce a diamino compound of the formula

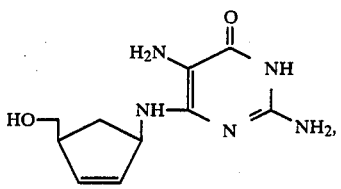

IV and (b) cyclizing such diamino compound by
(i) treating the compound with a formylating agent in a polar aprotic solvent in the presence of a non-aqueous acid catalyst under reflux, and
(ii) dehydrating the formylated compound with a mineral acid.

This invention still further provides a process for producing Carbovir, comprising cyclizing a diamino compound of the formula

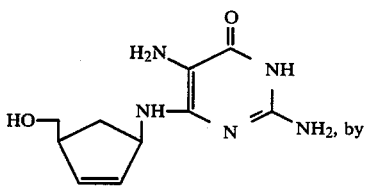

(a) treating such compound with a formylating agent in a polar aprotic solvent in the presence of a non-aqueous acid catalyst under reflux, and (b) dehydrating the formylated compound with a mineral acid.

The intermediates of formulas III and IV are novel compounds which are still further provided by this invention.

DESCRIPTION OF THE INVENTION

The novel processes and compounds of this invention are based upon the use of two principal starting materials, the compounds of formulae I and II. The compound of formula I can be prepared by refluxing methyl cis-4-acetamidocyclopent-2-enecarboxylate (Example 2, infra) in the presence of $Ba(OH)_2.8H_2O$ as described below. The preparation of the compound of formula II from commercially available 2-amino-4,6-dichloropyrimidine can be carried out as described by Constant et al. [J. Heterocyclic Chem. 22:1035 (1985)] and illustrated below (Examples 3 and 4).

Reaction of the compounds of formulae I and II to form the compound of formula III is carried out under anhydrous conditions in a polar aprotic solvent in the presence of a tertiary alkylamine. Suitable polar aprotic solvents include, e.g., dimethylacetamide, dimethyl sulfoxide and dimethylformamide. Tertiary alkyl amines that can be used include, e.g., trimethylamine, triethylamine, tributylamine and diisopropylethylamine. The displacement reaction can be carried out at a temperature of from about 0° to about 80° C. but is most conveniently run at room temperature.

While the most efficient use of reagents would dictate equimolar ratios of the compounds of formulae I and II and the tertiary amine, this displacement reaction is preferably run with about 1.5 equivalents of the compound of formula I to ensure the complete reaction of the compound of formula II and to facilitate the purification of the product.

Reduction of the nitro group of the compound of formula III to form the compound of formula IV is carried out in a mixture of aqueous sodium dithionite, a lower alkanol and a polar aprotic solvent, in about equal volume proportions. Lower alkanols that can be used include those having about 5 carbon atoms or less such as methanol, ethanol, propanol, isopropanol, butanol, etc. Suitable polar aprotic solvents are those described above. The reaction is conveniently carried out under reflux.

This reduction can be carried out at a temperature of from about 25° to about 100° C. but is conveniently carried out at reflux. It is preferably carried out using a ratio of about 2 to about 5 equivalents of dithionite to the compound of formula III, in aqueous DMF at reflux.

The diamino compound of formula IV thus produced was identified by its spectral properties but, as is characteristic of such compounds, was unstable. This compound is thus preferably prepared and used without prior isolation. Cyclization of the compound of formula IV is carried out in two steps.

Firstly, the amino group at the 5 position of the heterocyclic ring is treated with a formylating agent in a polar aprotic solvent in the presence of a non-aqueous acid catalyst. Suitable polar aprotic solvents are described above. Useful formylating agents include agents such as triethyl orthoformate, trimethyl orthoformate and dialkyl acetals such as dimethyl or diethyl acetal. A non-aqueous acid catalyst such as p-toluenesulfonic acid is employed, and the reaction is conveniently carried out under reflux. Formylation is conveniently run under conditions in which the formylating agent (e.g., triethyl orthoformate) is used as the solvent, the crude reduction product of formula IV is dissolved in a minimal amount of dimethylformamide, and the mixture is heated to reflux with the acid catalyst overnight.

Secondly, the formylated intermediate is dehydrated with a mineral acid such as hydrochloric acid, sulfuric acid or phosphoric acid, to complete formation of the new ring.

Although the foregoing reactions can be carried out through the use of the compound of formula I, it will be clear to those skilled in the art that another approach could also be taken. Instead, a compound of the formula

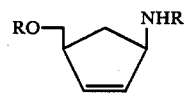

can be employed, wherein R is an acid-cleavable protecting group such as a trialkylsilyl group. Examples of such groups are t-butyldimethylsilyl, t-butyldiphenylsilyl, triphenylsilyl, triethylsilyl, diphenylmethylsilyl groups. Compounds of formula Ia can readily be prepared by reacting the compound of formula I with the corresponding trialkylsilyl chloride compound in the presence of a tertiary amine, in equimolar amounts, in a non-protic solvent such as dichloromethane, toluene, ether or tetrahydrofuran. The reaction can be carried out at a temperature of from about 0° C. to reflux, although room temperature is convenient. A compound of formula Ia can also be prepared by reacting the compound of formula I with hexamethyldisilazane at reflux.

A compound of formula Ia can then be reacted with the compound of formula II as described above to produce a compound of the formula

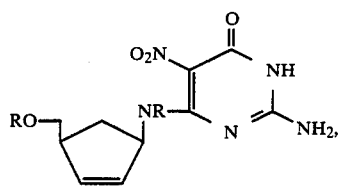

wherein R is as defined above. The compound of formula IIIa, in turn, can be reduced as described above to form a diamino compound of the formula

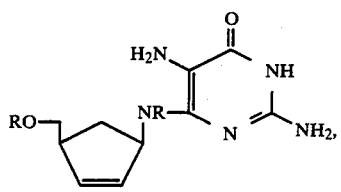

wherein R is as defined above. Such a compound of formula IVa, can be cyclized as described above, to produce Carbovir, with the trialkylsilyl groups being removed during the mineral acid treatment step.

The novel compounds of formulae IIIa and IVa are also a part of this invention.

The present invention can be more readily understood by reference to the following, nonlimiting examples.

EXAMPLE 1 p-Toluenesulfonyl Cyanide

A 12-liter 3-necked flask equipped with a mechanical stirrer, a scintered glass inlet tube, a thermometer and a gas exit tube connected to a 6N NaOH trap was charged with 997.9 g (4.60 moles) of p-toluene sulfinic acid, sodium salt (Aldrich), and 6.0 liters of water were added to dissolve the solids. An ice-salt bath was used to cool the solution below 0° C.

The valve of a cylinder containing 300 g (4.88 moles) of cyanogen chloride in a 35°–45° C. water bath was opened, and the gas was bubbled through the solution at a rate which maintained the temperature below 20° C. The bath was removed and the precipitated solids were stirred for an additional 30 minutes at room temperature, after which they were filtered and washed with three 2 liter volumes of water.

The wet solids were washed into a separatory funnel and dissolved in a minimum amount of carbon tetrachloride (about 750 ml). Then, 500 ml of hexanes were added to the solution. Solids began to form immediately. The solids were filtered and air dried to produce 684.4 g of pure p-toluenesulfonyl cyanide as white crystals, m.p. 47.5°–48° C. An additional 110 g of off-white solids were obtained from the mother liquors, m.p. 47°–48° C., for a total yield of 90%. The NMR was consistent with the expected structure.

EXAMPLE 2

Methyl cis-4-Acetamidocyclopent-2-enecarboxylate

A 5-liter flask was charged with 2.4 liters of freshly distilled cyclopentadiene and cooled to 0° C., when 340.9 g (1.882 moles) of tosyl cyanide were added in one portion and the suspension was stirred rapidly with a large magnetic stirrer without external cooling over 2 hours. The resulting light yellow translucent solution was placed on a rotary evaporator and evaporated (35° C./20 mm Hg) to a thick white granular residue.

The residue was cooled to below 0° C. in an ice-salt bath for 15 minutes under argon, 500 ml of cold (about 17° C.) glacial acetic acid were added, and the mixture was stirred for 10 minutes at ambient temperature. The acetic acid mixture, bright yellow in color, was cooled to about 5° C. in an ice-water bath. Six hundred milliliters of cold 4N HCl were added, and the mixture was stirred for 3 hours at 5° C., and then overnight at room temperature. The mixture gradually turned dark brown, an solids precipitated out.

The solution was filtered through Celite and washed with three 250-ml volumes of water. The combined aqueous layers were extracted with three 500-ml volumes of ether, and the combined ether layers were back extracted with 250 ml of water. The combined aqueous layers were placed in a rotary evaporator and concentrated (60° C./2mm Hg) to a yellow residue that was azeotroped in a rotary evaporator (45° C./20 mm Hg) with three 600-ml volumes of toluene, to give a dry amorphous residue.

The residue was dissolved in 1.5 liters of absolute methanol, HCl gas was bubbled through the solution for 5 minutes to saturate the solution, and the mixture was refluxed overnight. The then dark solution was placed in a rotary evaporator (40° C./20 mm Hg) and concentrated to a dark residue, to which 1.2 liters of pyridine were added. This dark solution was cooled in an ice bath to 5° C., when 750 ml of acetic anhydride were added. The bath was removed, and the solution was stirred overnight.

The dark solution was placed in a rotary evaporator (60° C./10 mm Hg) and evaporated to a dark brown syrup. The syrup was dissolved in 1.2 liters of $CH_2Cl_2$ and extracted first with two 1-liter volumes of water and then with three 500-ml volumes of 1.5N $H_2SO_4$, whereupon the organic layer was dried over anhydrous $K_2CO_3$.

After evaporation of the solvent in a rotary evaporator (35° C./20 mm Hg), the crude product crystallized, yielding 364.4 g. This crude product was adsorbed on 300 g of silica gel and placed on top of a short pad of 300 g of silica gel. Elution with EtOAC, after combination of the homogeneous fractions and evaporation of the solvent, gave 230 g of product, m.p. 57°–59° C. The overall yield was 67%. IR, NMR and MS were consistent with the expected structure. Analysis: Calculated for $C_9H_{13}NO_3$ C, 59.00; H, 7.15; N, 7.65. Found: C, 59.25; H, 7.05; N, 7.51.

EXAMPLE 3

2-Amino-6-chloro-4(3H)-pyrimidinone

A suspension of 250 g (0.1525 mole) of 2-amino, 4,6-dichloropyrimidine in 500 ml of 1N NaOH was heated to reflux. The solids gradually dissolved, and a complete solution formed after 4–5 hours. Acidification with about 70 ml of acetic acid gave a pH of 4 and precipitated a voluminous white solid that was filtered and washed with three 50-ml volumes of water. After drying in a vacuum over at 80° C./20 mm Hg, 21.75 g of product was obtained as fluffy white crystals, m.p. 260°–261° C., yield 99%. NMR, IR and MS were consistent with the expected compound. Analysis: Calculated for: $C_4H_4N_3OCl$: C, 32.37; H, 2.93. Found: C, 32.75; H, 2.81.

EXAMPLE 4

2-Amino-6-chloro-5-nitro-4(3H)-pyrimidinone

A solution of 64 ml of concentrated sulfuric acid and 64 ml of concentrated nitric acid was cooled to 0° to −5° C. in an ice-salt bath, when 11.75 g (0.0807 mole) of 2-amino-6-chloro-4-(3H)-pyrimidinone were added in small portions so that the reaction temperature did not exceed 10° C. After 45 minutes, all of the starting material was added. The mixture was stirred for 3 hours at 5°

C., when the mixture was poured over 400 g of ice and stirred for 1 hour at 5° C.

The precipitated solids were collected by filtration and washed with 35 ml of ethanol and 35 ml of ether and dried at 20° C./2 mm Hg overnight to produce 14.7 g of a yellow solid, m.p. 268° C. The yield was 87%. NMR, IR and MS were consistent with the expected compound. Analysis: Calculated for $C_4H_3ClN_4O_3 \cdot H_2O$: C, 23.04; H, 2.42; N, 26.87; $H_2O$ 8.64. Found: C, 22.70; H, 2.32; N, 26.82; $H_2O$ (Karl Fischer), 8.48.

EXAMPLE 5

(±)-(1α,4α)-4-[(2-Amino-5-nitro-6(1H)-pyrimidinone)-amino]-2-cyclopentenyl carbinol A mixture of 14.65 g (0.0743 mole) of methyl cis-4-acetamidocyclopent-2-enecarboxylate in 1.2 liters of water and 120.0 g (0.380 mole) of $Ba(OH)_2 \cdot 8H_2O$ was refluxed overnight. The following day, the mixture was cooled to room temperature, and excess dry ice was added to neutralize the mixture. The precipitated $BaCO_3$ was filtered out, and the aqueous solution was placed in a rotary evaporator at 60° C./2 mm Hg and concentrated to a light brown oil. The addition of 100 ml of absolute ethanol again precipitated solids that were filtered out, and the filtrate was concentrated as before to give a light brown oil.

The oil was dissolved in 100 ml of anhydrous DMF (dimethylformamide, dried by storage over 3 A molecular sieves for more than 30 days), and then 35 ml (0.25 mole) of triethylamine were added. Next, 11.6 g (0.055 mole) of 2-amino-6-chloro-5-nitro-4(3H)-pyrimidinone were added, and the homogeneous mixture was stirred overnight at room temperature. The mixture was placed in a rotary evaporator at 50° C./2 mm Hg and concentrated to a dark oil. Water (110 ml) was added to the dark oil, and the mixture was allowed to stand for 15 minutes and then filtered to collect the crude product as a brown solid. The solid was suspended in 300 ml of acetone and warmed to reflux, cooled to room temperature and filtered. The solids were washed with 25 ml of acetone.

After drying at 20° C./20 mm Hg, the solids weighed 12.65 g, had a m.p. 205°–207° C. and were homogeneous by TLC (4:1 $CHCl_3$:MeOH). The mother liquors were concentrated in a rotary evaporator to dryness and suspended in 15 ml of acetone. After washing and drying of the solid, an additional 0.66 g of equally pure material was thus produced, for a total yield or 90%. IR, NMR and MS were consistent. Analysis: Calculated for $C_{10}H_{13}N_5O_4$: C, 44.95; H, 4.90; N, 26.20. Found: C, 44.20; H, 4.75; N, 25.95.

EXAMPLE 6

Carbocyclic 2',3'-didehydro-2',3'-dideoxyguanosine

A solution of 13.32 g (0.0498 mole) of (±)-(1α,4α)-4-[(2-amino-5-nitro-6(1H)-pyrimidinone)-amino]-2-cyclopentenyl carbinol, 335 ml of DMF and 250 ml of methanol was heated to reflux, while a solution of 39.2 g of Na (Fisher) in 250 ml of water was added in one portion. The suspension gradually became homogeneous while it was refluxed for 30 minutes. TLC analysis (4:1 $CHCl_3$: MeOH) showed that all of the starting material had been consumed.

The mixture was cooled to room temperature and placed in a rotary evaporator at 55° C./2 mm Hg and concentrated to a solid tan residue. The residue was suspended in a mixture of 250 ml of anhydrous DMF and 250 ml of triethyl orthoformate with 1.0 g (0.0053 mole) of p-toluenesulfonic acid·$H_2O$ and heated to reflux overnight under argon. The mixture was then placed in a rotary evaporator (45° C./2 mm Hg) and concentrated to a dark brown solid residue that was dissolved in 500 ml of 0.5N HCl and stirred for 3 hours at room temperature.

The aqueous solution was placed in a rotary evaporator (45° C./2 mm Hg) and concentrated to a dark solid that was adsorbed onto a 300 g pad of silica and eluted with 4:1 $CHCl_3$: MeOH to isolate the organic portion. About 15 g of an orange solid were obtained. This solid was chromatographed on flash silica (30–40μ) to give 5.2 g (40%) of product Carbovir, m.p. 245°–246° C. IR, NMR and MS were consistent. Analysis: Calculated for $C_{11}H_{13}N_5O_2$: C, 49.80; H, 5.69; N, 26.90; $H_2O$, 6.78. Found: C, 49.91; H, 5.10; N, 26.36; $H_2O$ (Karl Fischer), 6.30.

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. (±)-(1α,4α)-[(2-Amino-5-nitro-6(1H)-pyrimidinone)-amino]-2-cyclopentenyl carbinol.

2. (±)-(1α,4α)-4-[2,5-Diamino-6)1H)-pyrimidinone)-amino]-2-cyclopentenyl carbinol.

3. A compound of the formula

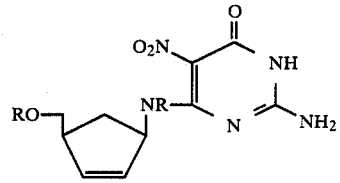

wherein R is an acid-cleavable protecting group.

4. The compound of claim 3 in which the protecting group is a trialkylsilyl group.

5. A compound of the formula

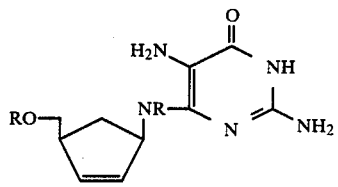

wherein R is an acid-cleavable protecting group.

6. The compound of claim 5 in which the protecting group is a trialkylsilyl group.

* * * * *